United States Patent [19]

Hetrick

[11] 4,272,330
[45] Jun. 9, 1981

[54] TRANSIENT MODE OXYGEN SENSOR AND METHOD

[75] Inventor: Robert E. Hetrick, Dearborn Heights, Mich.

[73] Assignee: Ford Motor Company, Dearborn, Mich.

[21] Appl. No.: 126,747

[22] Filed: Mar. 3, 1980

[51] Int. Cl.³ .............................................. G01N 27/58
[52] U.S. Cl. ................... 204/1 T; 204/195 S
[58] Field of Search .......................... 204/195 S, 1 S; 123/438, 489; 324/71 R

[56] References Cited

U.S. PATENT DOCUMENTS

| | | | |
|---|---|---|---|
| 2,999,379 | 9/1961 | Beard et al. | 73/23 |
| 3,100,868 | 8/1963 | McAfee | 324/33 |
| 3,311,454 | 3/1967 | Kemeny et al. | 23/254 |
| 3,347,635 | 10/1967 | McKee | 23/232 |
| 3,514,377 | 5/1970 | Spacil | 204/1 T |
| 3,654,112 | 4/1972 | Beekmans et al. | 204/195 S |
| 3,698,384 | 10/1972 | Jones | 128/2.07 |
| 3,857,771 | 12/1974 | Sternberg | 204/195 B |
| 3,907,657 | 9/1975 | Heijne et al. | 204/195 S |
| 3,923,624 | 12/1975 | Beekmans et al. | 204/195 S |
| 3,948,081 | 4/1976 | Wessel et al. | 73/23 |
| 4,101,403 | 7/1978 | Kita et al. | 204/195 S |
| 4,112,893 | 9/1978 | Anzai | 123/119 EC |
| 4,121,548 | 10/1978 | Hattori et al. | 123/32 EE |
| 4,135,381 | 1/1979 | Sherwin | 73/23 |
| 4,147,513 | 4/1979 | Bienkowski et al. | 23/232 E |
| 4,148,211 | 4/1979 | Sawa et al. | 73/23 |
| 4,169,440 | 10/1979 | Taplin | 123/119 EC |

Primary Examiner—G. L. Kaplan
Attorney, Agent, or Firm—Peter Abolins; Clifford L. Sadler

[57] ABSTRACT

This specification discloses a device to determine the partial pressure of oxygen in a gaseous atmosphere. The device, which is immersed in the atmosphere, is constructed to define an enclosed volume in which the atmosphere can be established by means of a small leak. The enclosing structure contains two partitions, a pump cell and a sensor cell, which can conduct oxygen ions and act as electrochemical cells. When attached to an external power supply, the current $I_P$ drawn through the pump cell either adds or removes (from or to the ambient) gaseous oxygen from the volume. As a result of the pumping action, an EMF ($V_S$) develops across the sensor cell which can be used to measure the change in oxygen partial pressure in the volume relative to the ambient. In a transient mode, a voltage step is applied to the pump cell removing (adding) oxygen from (to) the volume. The rate of change of $V_S$ with respect to time at the instant of the voltage step is measured. This time derivative is inversely proportional to oxygen partial pressure.

11 Claims, 7 Drawing Figures

TRANSIENT MODE OXYGEN SENSOR AND METHOD

BACKGROUND OF THE INVENTION

1. Field of the Invention

This invention relates to determining the concentration of oxygen in a gaseous atmosphere.

2. Prior Art

U.S. Pat. Nos. 3,907,657 to Heijne and 3,514,377 to Spacil et al relate to the measurement of oxygen $O_2$ concentrations using solid electrochemical devices. For applications at elevated temperatures (>500° C.), for example, as might be encountered in the exhaust gases of furnaces or automobiles, the active material in these devices may be ceramic zirconium dioxide suitably adapted for the conduction of $O^=$ ions. Electrochemical cells made from this material are suitable at elevated temperature for oxygen sensing and pumping applications.

The mode of operation of the Heijne device can be described as an oxygen counting mode in which oxygen partial pressure is determined on a sampling basis. A constant current (or equivalent means) is applied to an electrochemical cell which forms part of the enclosure of a volume for a period of time, $t_p$ for the purpose of electrochemically pumping out most of the oxygen from that volume. The ambient atmosphere had established itself within the volume prior to the pump out by means of a leak. An additional electrochemical cell, which serves as a sensor of the reduced oxygen partial pressure within the volume and which also constitutes a portion of the enclosure, provides a signal indicating when oxygen has been sufficiently depleted from the volume (see FIG. 4 of Heijne). Knowing the temperature, enclosed volume and the pump out current and time allows one to calculate the number of oxygen molecules within the enclosure from the ideal gas law. The number of oxygen molecules is in turn proportional to the desired oxygen partial pressure. If a constant pump current is used, the pump-out time $t_p$ is proportional to the oxygen partial pressure. If a constant current is not used, then the integral of the pump-out current over the pump-out time is proportional to the oxygen partial pressure.

The Heijne device can provide an output which is linearly proportional to the oxygen partial pressure. This is superior, for example to single oxygen concentration cells used as sensors which give an output (EMF) proportional to the natural logarithm of the oxygen partial pressure ln ($P_{O_2}$).

A potential disadvantage of the Heijne device is response time. For this measurement procedure, the leak connecting the ambient to the enclosed volume must be small so that during the pump out of oxygen, no significant amount of oxygen leaks into the volume to cause an error in the count of molecules (i.e., to erroneously increase $t_p$). However, if the leak is made small, it may take a long time, for the ambient to reestablish itself within the volume after a pump out. If the changes in the oxygen partial pressure in the ambient occur rapidly with respect to this time, then the device would not be able to follow these changes with repetitive operation.

U.S. Pat. Nos. 3,923,624 to Beckmans et al, 3,654,112 to Beckmans et al, and 3,907,657 to Heijne et al describe tubular ceramic structures for measuring and controlling the composition of oxygen in a carrier gas. In some cases a pump cell and a sensor cell are used. U.S. Pat. Nos. 3,923,624 and 3,654,112 teach devices to be used primarily to dose a gas with oxygen to a constant partial pressure. Measurement of the dosed gas is made by a standard technique using a zirconium dioxide oxygen concentration cell to be sure that the dosed gas contains the correct amount of oxygen. The sensitivity of the concentration cell to the oxygen partial pressure is low, being proportional to the natural logarithm of the oxygen partial pressure. This purpose is divergent from the purpose of measuring with high sensitivity the oxygen partial pressure in a feedgas. There is no suggested application of these devices for an auto exhaust.

In the case of the teachings of U.S. Pat. No. 3,698,384 to Jones, the purpose is to measure oxygen partial pressure in a feedgas. This is done by measuring the pumping current while holding the sensor cell voltage a constant. However, to achieve a result in the disclosed open ended tubular structure made from zirconium dioxide, the flow rate of the feedgas must be kept constant. If the flow rate should attempt to vary, there is a relatively elaborate flow control circuit to keep the flow rate constant. This scheme, which also employs a reference atmosphere, is relatively unsuitable for application in an auto exhaust where the exhaust flow rate would change substantially with RPM.

U.S. Pat. Nos. 3,347,635 to McKee and 3,857,771 to Sternberg both describe oxygen sensing procedures or devices wherein the taking of a first derivative of an output signal either determines the oxygen partial pressure or can yield information about the medium which contains the oxygen. Neither device would be suitable for the continuous or repeated determination of the oxygen partial pressure in a variable, high temperature environment like that occurring in an automotive exhaust.

FIGS. 1 and 2 of the drawings illustrate a known oxygen pumping sensor in which ionically conducting zirconium dioxide with thin platinum electrodes 2 and 3 form an electrochemical pump cell which with additional ceramic structure 4 define an enclosed volume 6. The ambient atmosphere can establish itself within the volume by means of a leak opening 5. A battery 7 is attached to the electrodes by means of lead wires 8 and 8'. A voltmeter 10 and ammeter 9 are provided to determine the voltage drop across the pump cell and the current flowing through it. Although similar in structure to FIG. 5 of U.S. Pat. No. 3,907,657, the operation is different. Here one applies a pump voltage V to remove oxygen from an enclosed volume 6 until the pump current saturates. The saturated current is proportional to oxygen concentration. This saturation property is shown in FIGS. 3 and 4.

This is a steady-state device. When steady state is reached, the flow of oxygen through a leak opening 5 equals the pump current times a proportionality constant. The current saturates at a voltage greater than about 0.5 V because the leak in combination with the platinum electrode 2, the cathode, will only allow a limited (saturated) amount of oxygen to enter and be electrochemically pumped from the volume per unit time. The device has the advantage of giving an output signal (the value of the limiting current) which is linearly proportional to the desired ambient oxygen partial pressure. However, to the extent that the saturated current value depends on the detailed properties of electrode 2, the device calibration may be subject to drift as these detailed properties may change during the sintering and wear of this thin layer.

An important application of high temperature oxygen sensors is in the determination of the stoichiometric air-fuel mixture in the exhaust gases of hydrocarbon fired furnaces or engines such as automobile internal combustion engines. The stoichiometric mixture is one in which the mass of air pressure contains just enough oxygen to react with the mass of hydrocarbons present so that there is the minimum amount of both oxygen and hydrocarbons remaining. For common automotive gasoline, the air fuel ratio (A/F=mass of air/mass of fuel) at the stoichiometric point is approximately 14.6. If, for example, an engine were running lean of stoichiometry (e.g., an air-fuel ratio greater than 14.6, there would be an excess of air in the "charge" and the exhaust gas would contain a substantial oxygen partial pressure. If rich operation were occurring, e.g., an air-fuel ratio less than 14.6, the exhaust gas would contain unreacted or partially reacted hydrocarbons and very low oxygen partial pressure. In particular, the equilibrium oxygen partial pressure in the exhaust gas can change by a great amount (as much as 20 orders of magnitude) as one moves from lean to rich operation. This large change forms the basis for detecting the stoichiometric air-fuel ratio with an exhaust gas oxygen sensor. The electrical output of such a sensor can then be fed back to an electrically controllable carburetor or fuel injection system for maintaining engine operation always at the stoichiometric point. Depending on engine type, operation at this point frequently offers a reasonable compromise for minimizing regulated exhaust gas emissions and maximizing engine performance.

There are known high temperature oxygen sensors utilizing oxygen electrochemical concentration cells (usually made from zirconium oxide) and requiring the use of a reference atmosphere (usually air) which are suitable for determining the stoichiometric air-fuel ratio. These devices give an output (EMF) proportional to natural logarithm of the oxygen partial pressure. Despite their low sensitivity to oxygen partial pressure, the large change in oxygen partial pressure at the stoichiometric point allows their useful implementation.

For some engines it is useful to operate lean of the stoichiometric A/F for the purpose of reducing fuel consumption. Oxygen partial pressure varies in a systematic way in the lean region and this can form the basis for determining lean A/F. The exact knowledge of lean A/F would be useful to fully implement a lean burn engine strategy which would maximize fuel economy and engine performance and minimize regulated emissions. However, the variation in oxygen partial pressure in the appropriate lean A/F region, e.g., air-fuel ratios greater than 16, is not large, (in comparison to the changes occurring near stoichiometry) so that suitable oxygen sensors with sensitivities greater than the natural logarithm of the oxygen partial pressure are desirable for accurate measurement in the desired A/F range. These are some of the problems this invention overcomes.

SUMMARY OF THE INVENTION

In accordance with an embodiment of this invention, a ceramic electrochemical structure with associated external circuitry is capable of measuring oxygen partial pressure in a high temperature surrounding environment such as may be found in an automotive exhaust. The structure includes two oxygen ion ($O^=$) conducting electrochemical cells, a pump cell and a sensor cell, which in part provide the enclosing structure of a nearly enclosed volume. After an ambient atmosphere of unknown but desired oxygen partial pressure has established itself within the volume by means of a leak, a voltage or current step is applied by the external circuit of the pump cell so as to electrochemically withdraw oxygen from the enclosed volume and inject it into the surrounding ambient. The ensuing reduction in oxygen partial pressure within the enclosed volume causes an electromotive force (EMF), increasing in time, to develop across the sensor cell. It is found experimentally that the first derivative of the sensor EMF with respect to time, evaluated at or near the initiation of the voltage step is inversely proportional to the first power of the desired oxygen partial pressure. This inverse relationship is the basis of sensor operation with much higher sensitivity than the logarithmic dependence offered by the more common oxygen concentration cell devices. The proportionality constant contains the absolute temperature and the value of the pump cell current at the start of the voltage step which must either be separately measured or otherwise maintained constant within acceptable limits.

The sensor cell EMF is increased by a reduction in oxygen pressure within the volume. For a given initial pump current, which is proportional to the number of oxygen molecules/sec withdrawn from the volume, the rate of reduction in interior oxygen pressure is greatest, and hence the rate of increase in the sensor EMF the largest, when the initial oxygen pressure within the volume is the least.

In a similar way, the polarity of the pump cell voltage can be reversed so that oxygen is pumped into the enclosed volume from the ambient. The initial slope of the sensor cell voltage can again be used to determine oxygen partial pressure except that the sign of the slope will be reversed.

In operation, the voltage step would be maintained just long enough for the derivative measurement to be made. At that point, the applied voltage would be relaxed so that a new ambient condition could establish itself within the volume before repeating the procedure. This measurement procedure is particularly advantageous because the calibration of the device is to some degree independent of the size of the leak thus allowing for some variability in manufacture, or wear in use, without affecting accuracy. The reason for this is that the derivative measurement is made at the start of the pump out when the leakage rate (occasioned by any difference in oxygen partial pressure between ambient and volume) is minimal. For the same reason, the device could be operated with a relatively large leak, which in combination with a short measurement time would result in high repetition rates or small response times.

DETAILED DESCRIPTION OF THE INVENTION

This disclosure teaches a solid electrochemical device, attached circuitry and a measurement technique for measuring oxygen partial pressure in a high temperature environment such as may be found in an automotive exhaust. In the latter environment as an example, the electrical output of the device which is related to the desired partial pressure may be used in the feedback control of the air fuel ratio of the automotive engine especially under lean operating conditions.

Figure 1:
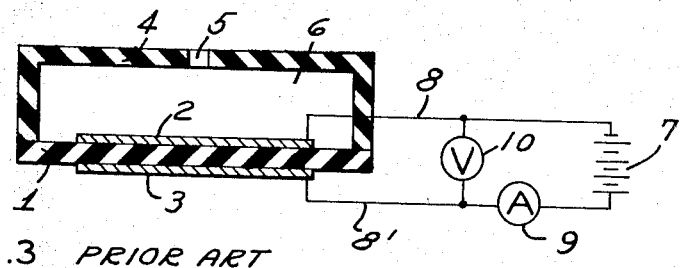
FIGS. 1 through 4 are prior art drawings with FIGS. 1 and 2 showing the construction of an electrochemical oxygen sensing device and FIGS. 3 and 4 show graphical representation of characteristics of the device.
Figure 2:
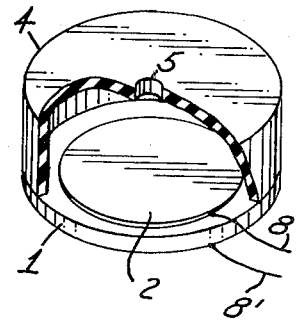
Figure 3:
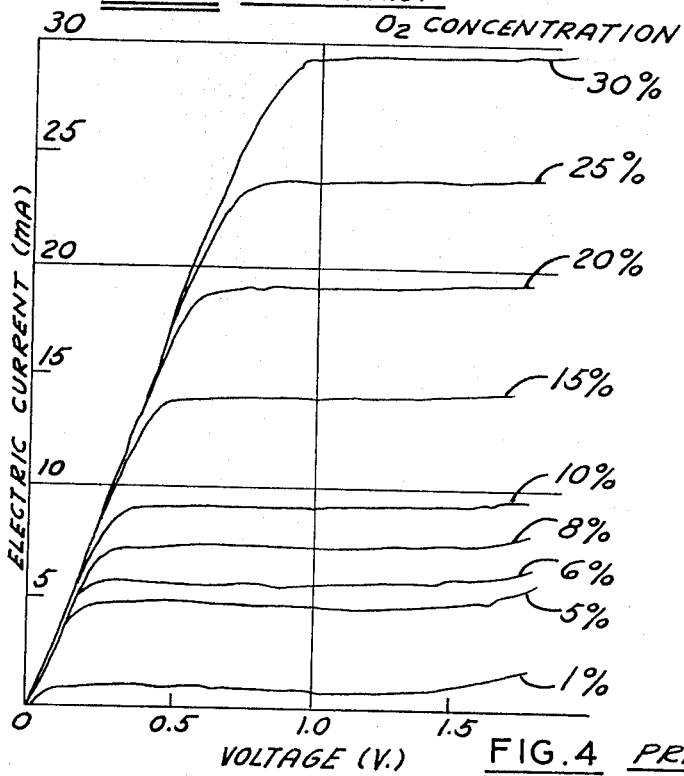
Figure 4:
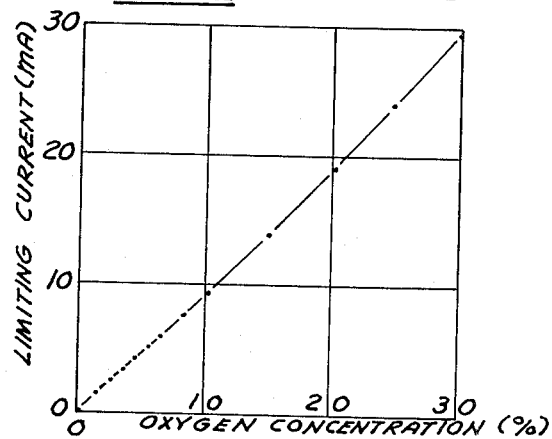
Figure 5A:
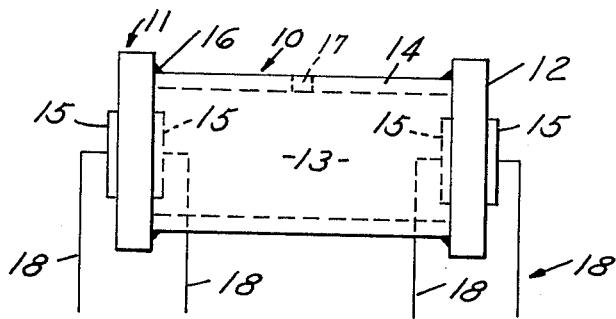
FIG. 5a is a schematic diagram of a portion of a device in accordance with an embodiment of this invention.
Figure 5B:
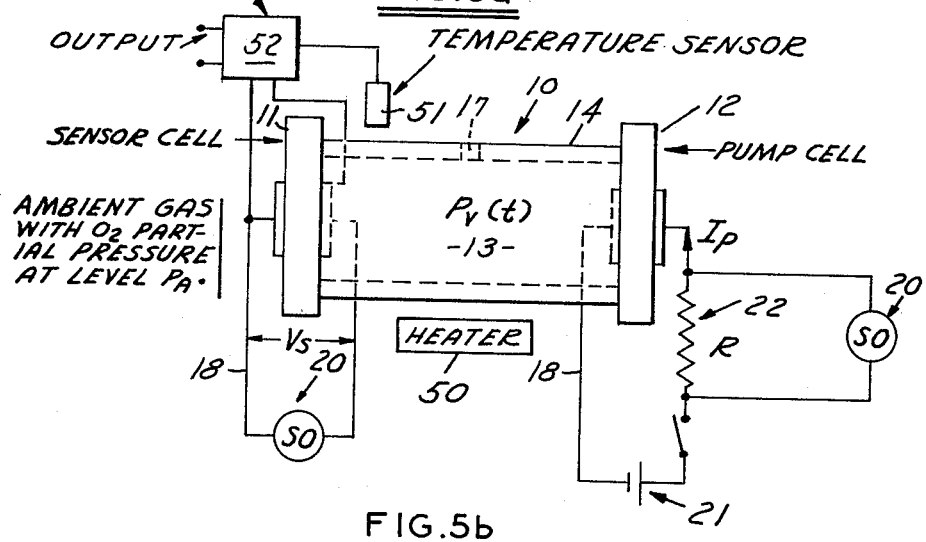
FIG. 5b is a schematic diagram similar to FIG. 5a with the addition of external circuitry for the measurement of oxygen partial pressure in an ambient gas.

As shown in the embodiment of FIGS. 5a and 5b, an electrochemical device 10 includes two platelets or cells 11 and 12, of zirconium dioxide suitably adapted for the conduction of oxygen ions. Such a solid ionic conductor is called a solid electrolyte. Electrodes 15 are attached to opposite faces of each of platelets 11 and 12 to form electrochemical cells. The right hand cell is termed a pump cell 12 and the left hand cell a sensor cell 11 to reflect their functions as will be described below. The device is symmetric and the functions of the cells could be reversed. The electrodes consist of platinum films (applied typically with platinum pastes or by sputtering techniques) with a typical thickness of one micron, or other materials suitably adapted for the purpose.

Lead wires 18 are affixed to each electrode 15 so that external circuitry may be applied to the cells. Using glass frits or ceramic glue 16 the zirconium dioxide platelets are joined by a hollow, non-porous ceramic tube or cylinder 14 to define an enclosed volume 13. The joining is effected so that one electrode from each cell will be within the enclosed volume. A small hole 17 can be drilled into ceramic tube 14 to allow the ambient atmosphere to establish itself within the volume. Alternatively, the seals between the zirconium dioxide and the tube 14 can be made somewhat leaky for the same purpose. The cells should be operated at an elevated temperature (greater than approximately 500° C. and typically 800° C.) so that the electrolyte is suitably conducting. Other embodiments may incorporate other oxygen ion conducting solid electrolytes (e.g., cerium dioxide adapted for the purpose) which can perform the desired electrochemical functions at lower temperatures. The device 10 is completely immersed in the atmosphere whose oxygen partial pressure is to be determined.

The electrical attachments are shown in FIG. 5b. A storage oscilloscope 20 or other voltage recording device is connected to the lead wires 18 of sensor cell 11 while a battery 21 in combination with a switch 23 (or equivalent means such as a voltage pulse generator) is connected to lead wire 18 of pump cell 12 through a current measuring resistor 22. A storage oscilloscope or other voltage recording device is used to record the voltage drop across the resistor 22 to determine the pump current $I_p$.

Electrical operation includes applying a voltage step to the pump cell, thereby defining an initial time $t=0$, with the proper polarity to withdraw oxygen from volume 13 and transfer it through the electrolyte to the surrounding ambient. As oxygen is electrochemically removed, the oxygen partial pressure within the volume $P_V(t)$ starts to fall relative to the oxygen partial pressure in the ambient, $P_A$. Note that $P_V(t=0)$ equals $P_A$. This difference in oxygen partial pressures provides the driving force for the leakage of oxygen into the volume from the ambient. For t greater than 0, the pumping rate as measured by $I_P$ decreases as the leakage rate rises in response to the growing difference between $P_A$ and $P_V$. Eventually, a steady state is reached where the leak rate equals the pumping rate.

During the transient reduction of $P_V$, an increasing EMF, $V_S(t)$, develops across the sensor cell 11 which is given by the familiar Nernst equation $$V_S(t) = (RT/4F) \ln (P_A/P_V(t)). \qquad (1)$$

Here T is the absolute temperature while R and F are the ideal gas and Faraday constants, respectively.

It is found that the slope, the first derivative with respect to time, of $V_S(t)$ evaluated in a region of time at or near zero has a constant value related to parameters of interest by Equation 2.

$$dV_S/dt(t=0) = T^2 I_P(t=0)/V P_A \qquad (2)$$

where V is the magnitude of the enclosed volume. The inverse first power dependence on $P_A$ forms the basis of an oxygen sensor with a much high sensitivity than the logarithmic dependence offered by the common, single oxygen concentration cell devices.

It may alternatively prove convenient to reverse the polarity of the pump cell voltage to cause oxygen to be pumped into the enclosed volume from the surrounding ambient. If this is done, the relation between the initial value of the slope of $V_S(t)$ is identical to that shown in Equation (2) except that the sign is changed. This procedure may alternately be used to sense $P_A$, although the remainder of the description will be described in terms of a pumping polarity which withdraws oxygen from the volume.

These findings can be closely accounted for by a theoretical model in which $P_V(t)$ is assumed to have a uniform value throughout the enclosed volume, and is determined by a simple rate equation analysis in which oxygen is removed from V at a rate proportional to $I_P$ and enters V at a leakage rate proportional to $P_A - P_V(t)$. The proportionality constant for the leakage rate defines the oxygen conductance of the leak and can be approximately determined by steady state pumping measurements.

To calibrate the device at a given temperature, a gas with known $P_A$ is established and the initial slope and pump current are measured so that the calibration constant C in Equation (3) can be determined.

$$dV_S/dt(t=0) = CI_P(t=0)/P_A \qquad (3)$$

Alternately, the pump cell external circuit could be designed so that $I_P(t=0)$ is always a constant value (as with a constant current source) which could be included in the calibration constant.

Figure 6:
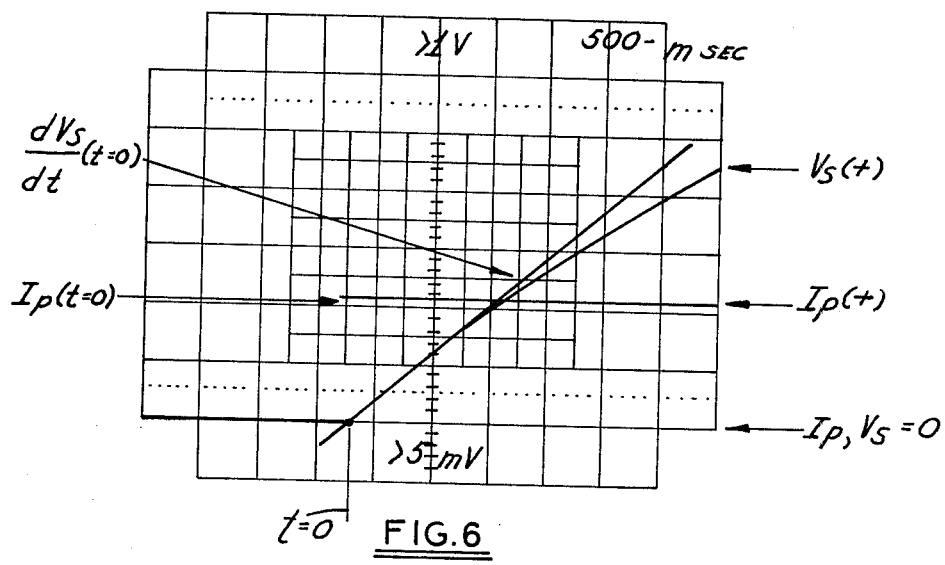
FIG. 6 is a graphical representation of current versus time during operation of the device illustrated in FIG. 5b.

Using the external circuit of FIG. 5b, the transient values of $V_S$ and $I_P$ would be recorded on a storage oscilloscope from which the initial slope and current could be measured for determining $P_A$. FIG. 6 gives an example of such an oscilloscope trace. In this example $T = 800°$ C., $I_P(t=0) = 20$ ma, $(dV_S/dt)_{t=0} = 8.3 \times 10^{-3}$ me V/sec and $P_A = 0.01$ atm.

After the slope measurement has been made, the pump current would be stopped (for example by opening the switch in FIG. 5b) and the ambient allowed to reestablish itself within the volume prior to making another measurement. To achieve the fastest possible repetition rate, it is desirable first to make the derivative measurement in the shortest time and second to utilize the largest practical leak conductance so that the ambient reestablishes itself quickly. The latter is promoted by maximizing the leak size and minimizing the leak volume. In this regard the present measurement technique is advantageous since the slope evaluated near $t=0$ does not depend, within certain limits, on the size of the leak which can thus be made large to allow an enhanced repetition rate. Further, some variability due to manufacturing tolerances, wear, or plugging can be tolerated. The reason for the weak dependence of the slope on leak size is that the measurement is made near $t=0$ when the leakage rate is very small. However, this independence is only approximate due to the small but finite time interval $\Delta t$ that will be required to make the slope measurement. Accordingly, to make an accurate measurement of $P_A$, the slope near $t=0$ must retain the constant value with the proportionalities shown in Equation (3) for the measurement interval $\Delta t$. In fact, this time interval varies as the leak size varies. For example, in the limit of increasingly large leaks, the allowed measurement interval for good accuracy would decrease. In this example, the decrease in measurement interval could be offset by increasing $I_P(t=0)$. In summary, the extent of the advantages offered by independence from the leak size are contingent upon the derivative measurement interval required by the external circuit.

As the above suggests, for a given range of $P_A$ values to be measured with a given measurement technique, device geometrical parameters such as enclosed volume and leak size as well as initial pump current can be optimized to allow the maximum practical measurement interval and repitition rates. The theoretical model discussed previously can serve as a useful guide in quantifying these parameters.

A further complication relates to the distance l between the enclosed surfaces of the pump and sensor cells. This arises because the onset of the rise in $V_S$ does not occur exactly at the instant the pump current is initiated but is delayed by a time which increases with increasing l. Delay occurs because oxygen is removed near the pump cell so that the reduced pressure within the volume is realized near the sensor cell electrode at a later time determined principally by l and the diffusion coefficient of oxygen in whatever gaseous species it may be mixed with. For example, with $l \sim 1$ mm the delay is on the order of 1 msec. Allowance must be made in the derivative measurement circuitry to accommodate this delay. The effect also causes a correction to the magnitude of the constant slope near $t=0$ which is accounted for empirically in the calibration constant.

To obtain a compact sensor package which might, for example, be used for an on-vehicle application, the external circuitry of FIG. 5b would be replaced by more specialized electronic circuitry to repetitively perform a partial pump out of the volume, measure $(dV_S/dt)_{t=0}$ and $I_P(t=0)$ as required, and provide a convenient output related to $P_A$ based on the relation of Equation (3). The exact nature of such circuitry would depend on the application and the necessary accuracy.

Equation (2) shows that the slope has a $T^2$ temperature dependence. To facilitate accuracy, it may be advantageous to account for the effects of changes in the temperature of the ambient atmosphere. This can be done in two ways. Firstly, referring to FIG. 5b, a heater 50 is used to maintain the temperature of device 10 and its adjacent gaseous surroundings within a sufficiently narrow range of values that a predetermined accuracy of the oxygen partial pressure measurement can be maintained with a single calibration constant appropriate for that narrow range of temperatures. As a given application requires, the "heater" may need to include a more elaborate electrical heating system in which a temperature sensor in the vicinity of the device, such as a thermocouple, provides the input to an electrical temperature regulator whose output activates the heater to a variable degree sufficient to maintain the temperature sensor output (or equivalently, the temperature) equal to some constant reference value preset in the regulator. Alternately, a temperature sensor 51 may be used to form one input of temperature correction circuitry 52 whose other input is $V_S$. The purpose of the circuitry is to correct $(dV_S/dt)_{t=0}$ for the changes in the device calibration constant as are occasioned by changes in the temperature. The output of the circuitry can be a convenient electrical quantity, such as a voltage, whose magnitude is proportional to oxygen percentage regardless of temperature. Depending on the application, the correction circuitry may need to encompass the facilities of a small computer.

Various modifications and variations will no doubt occur to those skilled in the various arts to which this invention pertains. For example, the electrodes may vary in shape from those described herein. Also, the configuration of the oxygen sensor and related external circuitry may be advantageously configured for use in an automotive exhaust. These and all other variations which basically rely on the teachings through which this disclosure has advanced the art are properly considered within the scope of this invention.

What I claim is:

1. An electrochemical apparatus for making a measurement of oxygen partial pressure in an ambient environment including other gaseous materials, said electrochemical apparatus including:

a solid electrochemical pump cell;

a solid electrochemical sensor cell;

an associated supporting structure which in combination with said pump and sensor cells defines an enclosed volume;

a leak orifice for providing communication between said enclosed volume and the ambient environment so that when said enclosed volume is immersed in an ambient environment containing a partial pressure of oxygen there is a tendency for the partial pressure of oxygen inside said enclosed volume to equalize with the partial pressure of oxygen of the ambient environment;

a first circuit means coupled to said pump cell to apply an electrical input to said pump cell, said electrical input being a voltage step function with an abruptly rising leading edge with respect to time having a polarity suitable for withdrawing oxygen from said enclosed volume, and said first circuit means including measuring means for measuring the magnitude of the current drawn through said pump cell as a result of the voltage step function;

a second circuit means coupled to said sensor cell for measuring an electrical output generated by said sensor cell in response to said electrical input at said pump cell, said electrical output having a relatively simple relationship to the ambient oxygen partial pressure so that said electrochemical apparatus can be used as a sensor of the oxygen partial pressure, said second circuit means being adapted to measure the first derivative with respect to time of the sensor voltage, as induced by the pumping action of said pump cell when the voltage step is applied to said pump cell, said voltage step rising in magnitude with respect to time faster than the sensor voltage; and said pump and sensor cells being formed of platelets of solid ionic conductors capable of conducting oxygen ions and including two electrode layers attached to opposing faces of each of said platelets, and lead wire attached to each of said electrodes for coupling said external circuit means to said pump and sensor cells.

2. An electrochemical apparatus as recited in claim 1 wherein:

said associated supporting structure includes a hollow tube of material which is impervious to gases and retains a structural rigidity at elevated temperatures found in the exhaust gases of an internal combustion engine; and said pump cell and said sensor cell being affixed to opposing ends of said tube by a mounting means said pump and sensor cells being affixed to said tube so that one of said electrodes of each of said cells forms a part of the surface adjacent to said enclosed volume.

3. An electrochemical apparatus as recited in claim 2 wherein said second circuit means includes processing means for processing the first derivative of a voltage change in accordance with an inverse relationship between the desired oxygen partial pressure and the first derivative, calibration constants, temperature data, and initial current in said pump cell, so that there can be presented a convenient electrical output related to the desired oxygen partial pressure.

4. An electrochemical apparatus as recited in claim 1 further comprising:

control means coupled to said first circuit means for repetitively applying and relaxing the voltage step and synchronizing the measurements of initial pump cell current and the voltage first derivative at said sensor cell so that the desired pressure measurement can be done at a variable repetition rate.

5. An electrochemical apparatus as recited in claim 1 further comprising a heater to maintain the temperature of said electrochemical structure and its adjacent gaseous surroundings so that a single calibration constant appropriate for the maintained range of temperatures can be used.

6. An electrochemical apparatus as recited in claim 1 further comprising:

third circuit means coupled to said second circuit means for measuring the temperature, T, in degrees Kelvin in the region of said sensor cell and correcting the output of said electrochemical apparatus for the dependence of that output on the temperature.

7. An electrochemical apparatus as recited in claim 1 wherein said first circuit means is adapted to apply a voltage step with a polarity to pump oxygen into said enclosed volume from the ambient, and said second circuit means is adapted to measure the reverse sign of the first derivative of the voltage of said sensor cell.

8. A method for making a measurement of oxygen partial pressure in an ambient environment having other gaseous material including the steps of:

establishing an enclosed volume with restricted access to the ambient environment, the enclosed volume being bounded by a solid electrolyte electrochemical pump cell and a solid electrolyte electrochemical sensor cell, and the restricted access being sufficient so that when the enclosed volume is immersed in an ambient environment containing a partial pressure of oxygen there is a tendency for the partial pressure of oxygen inside the enclosed volume to equalize with the partial pressure of oxygen of the ambient environment;

applying to the pump cell an electrical voltage step function with an abruptly rising leading edge having a polarity suitable for withdrawing oxygen from the enclosed volume;

measuring the magnitude of the current drawn through the pump cell as a result of applying the voltage step function;

measuring an electrical output generated by the sensor cell in response to the electrical input at the pump cell, the electrical voltage step function being chosen to rise in magnitude with respect to time faster than the electrical output; and calculating the oxygen partial pressure using an inverse relationship with the first derivative of the voltage measured at the sensor cell.

9. A method as recited in claim 8 further comprising the step of:

repetitively applying and relaxing the voltage step and synchronizing the measurements of initial pump cell current and the voltage at the sensor cell so that the desired pressure measurement can be done at a variable repetition rate.

10. A method as recited in claim 9 further comprising the step of:

maintaining the temperature of the enclosed volume and adjacent regions so that a single calibration constant appropriate for the maintained range of temperatures can be used.

11. A method as recited in claim 10 further comprising the step of:

measuring the temperature in the region of the sensor cell and correcting the measurement of the oxygen partial pressure for the dependence of the output on the temperature squared.

* * * * *